United States Patent [19]

Smith et al.

[11] Patent Number: 4,483,198

[45] Date of Patent: Nov. 20, 1984

[54] OSTEOCLAST FOR WHOLE BONE TESTING

[75] Inventors: Howard W. Smith, Lawrence, Kans.; Carl R. Kulp, Jr., West Chester, Pa.

[73] Assignee: The United States of America as represented by the Secretary of the Air Force, Washington, D.C.

[21] Appl. No.: 455,673

[22] Filed: Jan. 5, 1983

[51] Int. Cl.³ ............................................. G01N 3/00
[52] U.S. Cl. ...................................................... 73/794
[58] Field of Search .......................... 73/794, 795, 796

[56] References Cited

U.S. PATENT DOCUMENTS

| | | |
|---|---|---|
| 1,608,804 | 11/1926 | Moore . |
| 1,827,805 | 10/1931 | Watts . |
| 2,151,584 | 3/1939 | Bugatti .................................. 73/796 |
| 3,203,231 | 8/1965 | Klatchko ............................... 73/796 |
| 3,752,144 | 8/1973 | Weigle, Jr. ........................... 128/2 S |
| 3,866,607 | 2/1975 | Forsythe et al. .................. 128/92 R |
| 4,202,355 | 5/1980 | Loeffler ............................... 128/774 |
| 4,232,681 | 11/1980 | Tulaszewski ......................... 128/653 |
| 4,323,080 | 4/1982 | Melhart ................................ 128/774 |

OTHER PUBLICATIONS

Carl R. Kulp, Jr. & Howard W. Smith, "Mechanical Properties of Four Human Longbones", (Nov. 30, 1981).

Primary Examiner—Anthony V. Ciarlante
Attorney, Agent, or Firm—Donald J. Singer; Bobby D. Scearce

[57] ABSTRACT

A novel test device particularly adaptable for simultaneously applying bending and torsion loads to whole bone specimens is provided, which comprises a substantially rigid support frame, first and second supports pivotally mounted to the frame for supporting the specimen therebetween, transverse loading (bending) means supported by the frame intermediate the supports for applying loads to the specimen at predetermined locations therealong, a torsion loading means supported on the frame for applying torque to said specimen by rotation of the second support, and force sensing means for measuring the bending and torsion loads and providing an output signal proportional thereto.

3 Claims, 5 Drawing Figures

OSTEOCLAST FOR WHOLE BONE TESTING

RIGHTS OF THE GOVERNMENT

The invention described herein may be manufactured and used by or for the Government of the United States for all governmental purposes without the payment of any royalty.

BACKGROUND OF THE INVENTION

The present invention relates generally to the field of materials testing devices, and more particularly to a novel testing machine configured to simultaneously apply bending and torsion loads to a test specimen, the invention herein having particular utility in studies related to the mechanical properties and fracture patterns of bones.

In the studies of the strength, mechanical behavior and fracture patterns of specimens comprising whole bones, and specifically the human long bones including the radius, ulna, femur, tibia, humerus and fibula, the use of simplified mathematical models approximating bone structure are inadequate to predict responses of bone specimens to mechanical loads. Although a great deal of data on the geometry of bones exists in the literature, this information is of little use in the calculation of bone strength or in the prediction of fracture patterns of whole bone samples for practical applications because of the anisotropy and heterogeneity which characterize whole bone structure. Therefore, accurate data on the response of bones subjected to various predetermined loading conditions must necessarily be obtained experimentally.

The correlation of information gained from empirical determinations of loading characteristics and fracture patterns of bone specimens may be extremely useful to an orthopedist in determining what kind of load is responsible for a particular fracture and in providing proper treatment accordingly or in designing appropriate prostheses. Cumulative information gained through fracture studies using the osteoclast of the present invention would be useful to human factors engineers, biomedical engineers, physicians, and the like in the design of equipment, such as aircraft cockpits and ejection seat mechanisms, automobile safety equipment, and the like to avoid to the extent possible any potential trauma to which the user may be subjected.

The present invention provides a test device capable of applying bending loads or torsional loads, or any desirable combination thereof, to test specimens comprising bones. The device is uniquely configured to provide means to establish the fracture patterns which are associated with bending failures, torsional failures and failures of combined bending and torsion to provide data on the correlations between fracture patterns and the magnitudes of contributing loads, to enable the application of predetermined stress states at selected locations on the surfaces of a test bone specimen; and to provide data on the gross material behavior of bone tissue, micro-mechanical fracture topography, and fracture mode. Although the test device of the present invention is particularly suited for testing human longbones, it can be used without modification for testing a wide variety of animal bones or other structures of similar shapes. With slight modifications, structures of other types, such as vertebral column segments, short or flat bones, or the like may also be tested.

It is, therefore, an object of the present invention, to provide a novel testing device.

It is a further object of the invention to provide a testing device for simultaneously applying bending and torsion loads to a test specimen.

It is yet a further object of the invention to provide a device for applying bending and torsional loads simultaneously to a bone specimen for determining certain mechanical properties and fracture patterns of the bone.

These and other objects of the present invention will become apparent as the detailed description of certain representative embodiments thereof proceeds.

SUMMARY OF THE INVENTION

In accordance with the foregoing principles and objects of the present invention, a novel test device particularly adaptable for simultaneously applying bending and torsion loads to whole bone specimens is provided, which comprises a substantially rigid support frame, first and second supports pivotally mounted to the frame for supporting the specimen therebetween, transverse loading (bending) means supported by the frame intermediate the supports for applying loads to the specimen at predetermined locations therealong, a torsion loading means supported on the frame for applying torque to said specimen by rotation of the second support, and force sensing means for measuring the bending and torsion loads and providing an output signal proportional thereto.

DESCRIPTION OF THE DRAWINGS

The present invention will be more clearly understood from the following detailed description of representative embodiments thereof read in conjunction with the accompanying drawings wherein.

DETAILED DESCRIPTION

Figure 1:
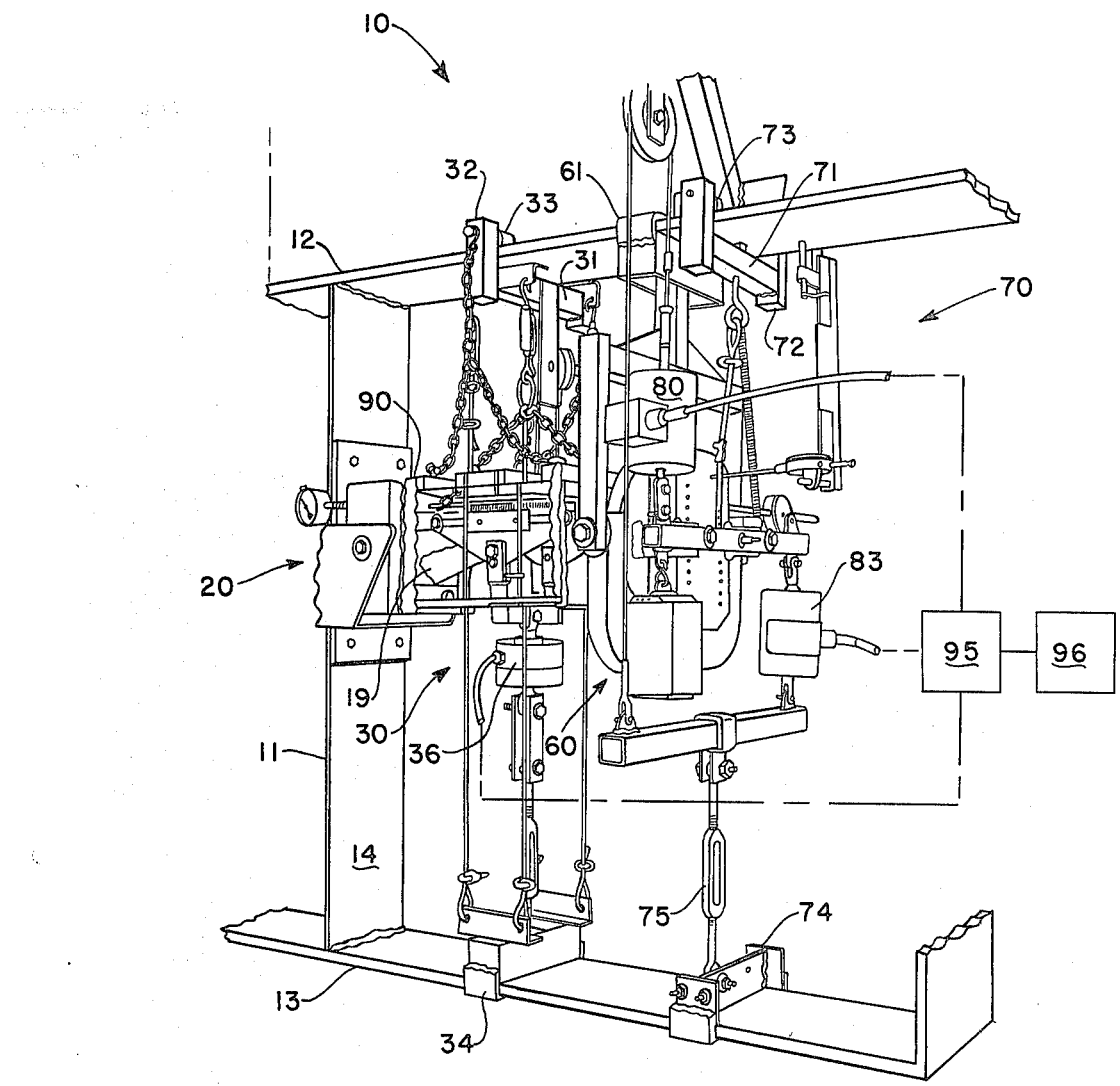
FIG. 1 is a perspective view of a representative embodiment of the invention herein.

Referring now to FIG. 1, shown therein is a schematic perspective view of a representative osteoclast 10 of the present invention. The machine depicted in FIG. 1 found particular utility in the studies described above of the mechanical strengths and fracture patterns characteristic of human long bones, the machine of the present invention providing the means for applying pure bending, pure torsion or combinations of bending and torsion to the bone specimens. It is understood at the outset, that, although the invention in a representative embodiment thereof was constructed and used as described herein to fracture bones as part of a study relating to bone structural analysis, the invention may be alternatively used, as would occur to one with skill in the field of this invention to apply bending and torsion loads to structures and materials of a wide variety.

The representative osteoclast 10, as depicted in FIG. 1 in all its component parts and auxiliary equipment as herein described in detail was configured to provide a moveable, self-contained testing machine. To this end, the osteoclast 10 and its component parts were supported on a welded, rigid I-beam frame 11, approximately three feet high by four feet wide, and supported on four castors and provided with leveling jacks as means (not shown) to provide mobility and stability to osteoclast 10.

Figure 3:
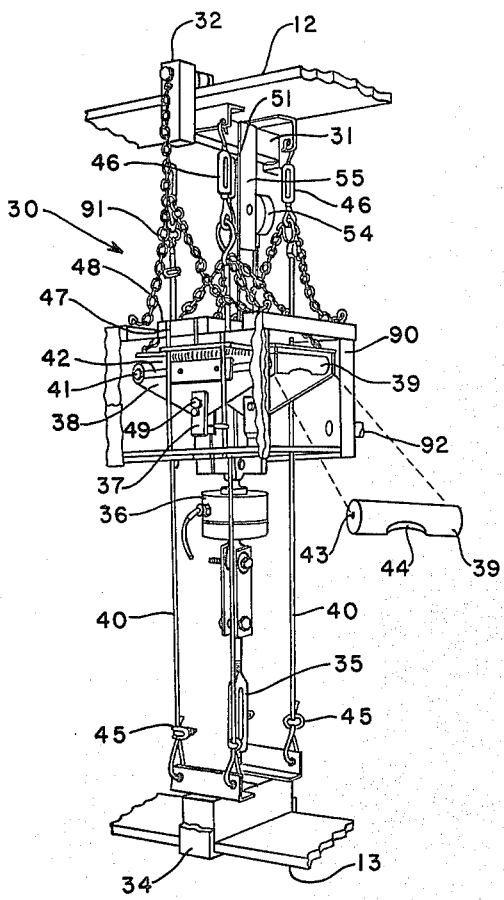
FIG. 3 is a perspective view of that portion of the device depicted in FIG. 1 comprising the bending load application mechanism thereof.
Figure 4:
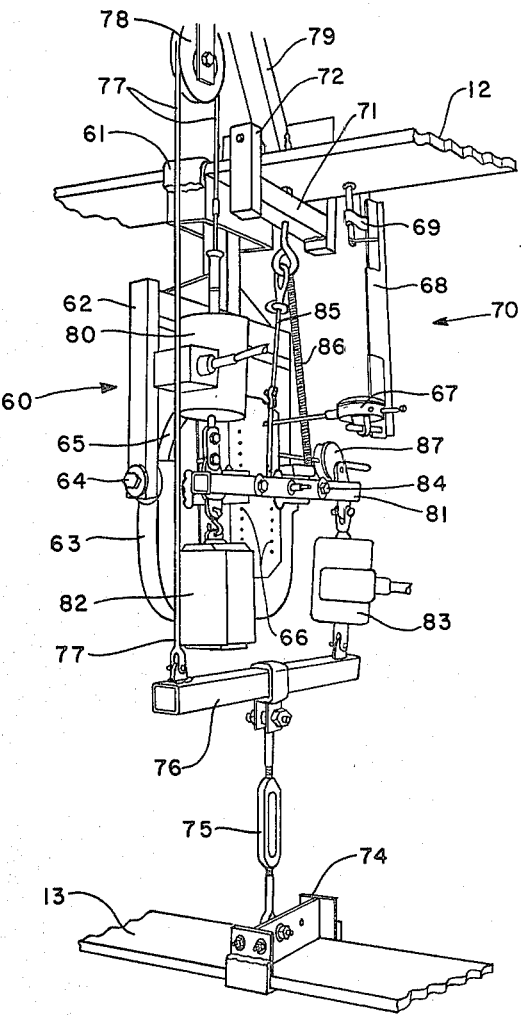
FIG. 4 is a perspective view of that portion of the device depicted in FIG. 1 comprising the suspended end clamp and torsion load application mechanism thereof.

As shown in FIG. 1, osteoclast 10 comprises five major component assemblies, viz., fixed end clamp assembly 20, bending load mechanism 30, suspended end clamp assembly 60, torsion load application mechanism 70 and humidity chamber 90, together with auxiliary electronics. The fixed end clamp assembly 20 is shown individually in FIG. 2. Bending load mechanism 30 and humidity chamber 90 are shown in FIG. 3, and torsion load mechanism 70 and suspended end clamp assembly 60 are shown in FIG. 4. The bending load application mechanism 30 is configured to be moveably supported on rollers 33 by upper beam 12 of frame 11, and clamp 34 on lower beam 13. Similarly, torsional load mechanism 70 is moveably supported between beams 12 and 13 of frame 11 by bridge 71 of trolley 72, rollers 73 and clamp assembly 74. Suspended end clamp assembly 60 is held relative to beam 12 using clamp assembly 61. All clamps 34, 74, and 61 were fabricated by welding together pieces of steel plate and angle steel and included bolts at each end to clamp to frame 11 in conventional fashion. Trolleys 32 and 72 were fabricated of one-inch square steel tubing in the shape of U assemblies and are supported on beam 11 by rollers 33 and 73 respectively, to allow rolling supports for mechanisms 30 and 70 on the flange of beam 12.

Figure 2:
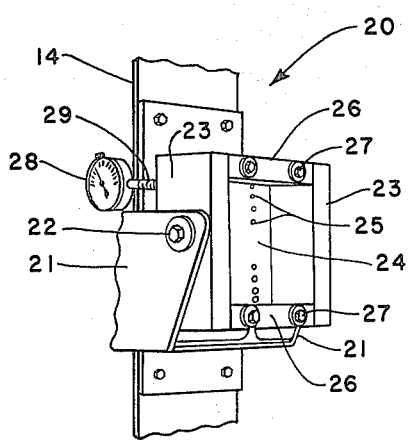
FIG. 2 is an enlarged perspective view of the end clamp of the FIG. 1 device for supporting one end of a bone specimen under test.

Referring now to FIG. 2, shown therein is a somewhat enlarged view of the end clamp assembly 20 of FIG. 1 for supporting one end of a bone specimen 19 under test, and configured to prevent rotation of bone 19 subjected to a twisting motion along its longitudinal axis under the influence of torsion load mechanism 70 as herein described. End clamp 20 is pivotally attached to the upright beam 14 of frame 11 through a pair of attaching plates 21. Bolts 22 pivotally support clamp 20 and ride inside a pair of oil impregnated bronze sleeve bearings (not shown) in the sides of clamp 20. Clamp 20 comprises a pair of two-inch wide by five-inch aluminum side plates 23 spaced approximately five inches and welded to a backplate 24. Backplate 24 has two vertical rows of threaded holes 25 (one such vertical row is visible in FIG. 2). Top and bottom plates 26 comprise machined aluminum plates each having a pair of holes drilled longitudinally therethrough to receive bolts 27 of sufficient length to engage selected threaded holes 25 to secure plates 26 to backplate 24 between sides 23, substantially as shown. Top and bottom plates 26 are positioned and secured to backplate 24 in any desired spacing depending on the selected spacing of holes 25 in backplate 24. In the osteoclast 10 built for bone 19 fracture studies hereinabove described, fixed end clamp assembly 20 is configured to provide selected spacings between plates 26 in $\frac{1}{2}$ inch increments from about one to about 5 inches. The selectivity of spacing of plates 26 provides a desirably wide range of cavity sizes defined by the sides and back of clamp 20 to receive one end of a bone specimen 19 for test. In addition, the confronting surfaces of plates 26 have shallow recesses machined thereinto on that portion of the surfaces adjacent backplate 24 to provide a positive grip on bone specimen 19 to prevent it from sliding out of clamp 20 as loads are applied. Further positive gripping of the ends of bone specimen 19 may be accomplished by casting the ends in an epoxy putty within an appropriate mold, and subsequently clamping the molded epoxy within clamp 20.

The clamp 20 pivots on its bearings about an axis substantially parallel to the plane of frame 11 and perpendicular to the axis of specimen 19 while reacting all loading situations on bone specimen 19, and, therefore, behaves as a simple support. A slope dial gage 28 measures the degree of pivoting of clamp 20. Because the center of gravity of the clamp 20 does not pass vertically through the pivot points (bolts 22), an end moment occurs that tends to oppose the bending moment as well as induce an unwanted load during torsion. To offset this moment, a compression spring 29 is inserted between the slope dial gage 28 and the backplate 24. This moment is considered to be significant only when testing slender specimens, such as the fibula.

The bending load application mechanism 30 (ref. FIGS. 1 and 3) provides a constant amplitude device which applies a bending load, transverse of the axis of specimen 19, by requiring increases in bending deflections at the load points along the bone diaphysis. A turnbuckle 35 in the mechanism 30 train generates the deflections and the load ensues as a result of the elastic behavior of the bending bone specimen 19. The tensile force developed in the system follows a path from the reaction point, clamp 34, through the turnbuckle 35, force sensing load cell 36, clevis/yoke 37, through the sides of the bending carriage 38 to aluminum rollers 39 which then transfer the load to the bone 19 surface. This tensile force along with the stabilizing cables 40 (when taut), assure the stability of the entire mechanism 30 throughout the operating range of osteoclast 10.

The variation in the lengths of the bones 19 tested required the construction of two bending carriages 38, having, respectively, an overall length of about 9 inches (22.86 cm) for testing the femurs, tibias and fibulas, and an overall length of about $5\frac{5}{8}$ inches (14.29 cm) for testing humeri. Each carriage 38 comprises three precut, premachined, and welded pieces of $\frac{1}{4}$ inch (6.35 mm) aluminum plate in the form of an inverted channel. The carriages 38 are $4\frac{1}{8}$ inches (10.48 cm) wide and serve as housings for two aluminum rollers 39 at each end thereof. To fasten the rollers 39 to the carriage 38, large bolts 41 pass through slots 42 in the sides of the larger carriage, and holes in the sides of the smaller carriage, and through axial holes 43 in rollers 39. The slots 42 in the larger carriage 38 allow a variety of roller 39 spacings between a maximum separation of about 7.94 inches (20.17 cm) and a minimum separation of about 4.83 inches (12.27 cm). The holes in the smaller carriage fix the spacing at about 2.7 inches (6.35 cm). Washers inserted between the carriage 38 sides and the ends of the rollers 39 prevent the two from binding. To keep each carriage 38 centered above the bone specimen 19, circular cuts 44 are provided on each roller 39 normal to, but below the mid-point of the roller 39 axis, substantially as shown in the exploded view of roller 39 within FIG. 3.

Four cables 40, each 0.125 inch (3.12 mm) in diameter, are used to guide the bending carriage 38 as the bending load is applied. Two cables 40 extend past the carriage 38 on each side from the clamp 34 to the trolley 32. Each cable 40 is fastened with a cable thimble and clip 45 to cross-members on the clamp 34 below mechanism 30 and to the eye of a turnbuckle 46 attached at its upper end to cross-members on trolley 32, substantially as shown. The turnbuckles 46 allow the cables 40 to be removed or stretched until taut. Normally, cables 40 are tensioned by suitable adjustment of turnbuckles 46 sufficient to prevent the cables 40 from deflecting more than 0.3 inch (7.62 mm) in any direction. Slots 47, machined into opposite edges of a thin steel plate 48 which is bolted to the top of the carriage 38, receive the cables 40 and guide the carriage 38, thus limiting its horizontal motion. The smaller carriage has these slots machined as an integral part of its top. Such restraint prevents the carriage 38 from sliding sideways off the bone specimen 19 or to and fro along its axis. Teflon ® tubing is provided as a covering on each cable 40 along the span of travel of the carriage 38 thereon to reduce friction and prevent cables 40 and carriage 38 from binding.

The yoke 37 assembly connects the bending carriage 38 to the load cell 36 and was made by welding pieces of strap iron together to form a U-shaped yoke with clevises at its ends. The clevises of yoke 37 are attached to the sides of the bending carriage 38 using a pair of cotter key and bolt fasteners 49. Load cell 36 is bolted to the bridge of yoke 37 and to turnbuckle 35, substantially as shown in FIG. 3.

Figure 3A:
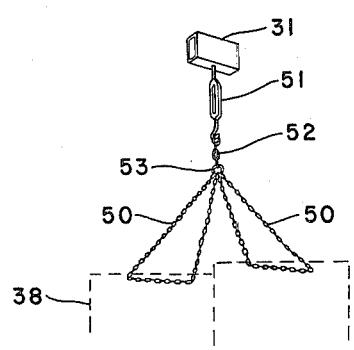
FIG. 3a is a view of a portion of the support configuration for the carriage of the bending load mechanism.

A pair of light chains 50 connected to the bridge 31 of trolley 32 using a turnbuckle 51 are used to suspend the bending carriage 38 above and out of the way of the bone specimen 19 (see FIG. 1) while the specimen 19 is clamped into osteoclast 10 for test. FIG. 3a is a view of the chains 50 configuration as they are disposed in place supporting carriage 38. As shown in FIG. 3a chains 46 assume in place the shape of two equal loops connected to a heavier chain 52 through an S hook 53, the heavier chain 52 being suspended from turnbuckle 51 attached to bridge 31 of trolley 32, substantially as shown. The elevation of the bending carriage 38 within frame 11 may be adjusted in a gross manner by inserting the lower hook of turnbuckle 51 into an appropriate intermediate link of the heavier chain 52 approximating the desired level of carriage 38, and then finely adjusted by turning the turnbuckle 51. Once the rollers 39 of the bending carriage 38 contact the surface of bone specimen 19 the heavier chain 52 is hooked on the turnbuckle 51 by the link on its free end. This provides enough slack in the light chain 50 to permit the carriage 38 to travel as bone specimen 19 deflects under the applied bending force, and, yet, prevents the entire train from collapsing when the bone specimen 19 breaks. By this arrangement, the bending carriage 38 is kept out of the way while a bone specimen 19 is clamped into place in the osteoclast 10, but allows the bending load mechanism including carriage 38 and rollers 39 to be conveniently lowered onto the bone 19 for testing.

Referring now to FIG. 4, shown therein individually are the suspended end clamp 60 assembly and the torsion load application mechanism 70 of the osteoclast 10 as depicted in FIG. 1.

The suspended end clamp 60 assembly is configured to support the end of bone specimen 19 opposite that supported by clamp 20 (see FIG. 1 and 2), in manner allowing torque to be applied to bone 19 along its longitudinal axis by torsion load mechanism 70. Clamp assembly 60 comprises a tubular steel yoke 62, an aluminum yoke 62 pivotally (about an axis substantially perpendicular to specimen 19) mounted to yoke 62 using a pair of bolts 64 riding in oil impregnated bronze bearings (not shown) in aluminum yoke 63, and an adjustable disc/clamp 65 configured to be received by yoke 63. Clamp assembly 60 is suspended from beam 12 of frame 11 by clamp 61 connected to the mid-point of the bridge of tubular steel yoke 62 as shown in FIG. 4. Adjustability of clamp 61 along the span of beam 12 allows a variety of bone specimen 19 anatomical lengths to be accommodated. Aluminum yoke 63 is machined from a solid piece of aluminum stock to receive and hold the disk/clamp 65. The disk/clamp 65 is fabricated from several pieces of aluminum stock machined and then welded together to form a single unit. The periphery of the disk 65 and the receiving surface, or race, in the aluminum yoke 63 were machined on a lathe to a sliding fit tolerance. Flanges on the front and back of the race prevent the disk 65 from sliding out of the yoke 63. When assembled, the disk 65 slides in the race of yoke 63 on a film of lithium grease.

A clamp (not shown in FIG. 4) is attached to disk 65 on the side thereof confronting end clamp 20 (see FIG. 1), and is configured substantially identically to clamp 20, having adjustable clamping means in substantially the same dimensional ranges as clamp 20.

Suspended end clamp assembly 60 as just described is pivotally suspended by the clamp 61 from upper beam 12 to allow modest horizontal movement of the assembly 60 in the direction of the bone 19 axis to eliminate tensile forces that otherwise could be induced during bending.

The torsion load application mechanism 70 as shown individually in FIG. 4 comprises a constant amplitude loading means for applying torque to the bone specimen 19 within osteoclast 10. The mechanism 70 includes a clamp 74 anchored to lower beam 13 for providing a reaction point in applying torque, and a turnbuckle 75 adjustably interconnecting clamp 75 to a centering bridge 76. One end of a cable 77 is attached to one end of bridge 76 and passes over a pulley 78 and supported thereby on upper beam 12 of frame 11. The second end of cable 77 supports a force sensing means in the form of load cell 80 connected to one end of torque bar 81, and a balancing counterweight 82. A second load cell 83 interconnects the second end of torque bar 81 and centering bridge 76 as shown. Torque bar 81 is bolted, in a spaced relationship using a pair of spacer blocks, to the body of disk/clamp 65 of suspended end clamp assembly 60 using a pair of bolts 84 intermediate the ends of torque bar 81 and engaging mating tapped holes 66 provided in disk/clamp 65, substantially as shown. Torque bar 81 is supported at its midpoint by a cable 85 attached to the bridge 71 of trolley 72.

A compensating spring 86 interconnects bridge 71 of trolley 72 and torque bar 81 to assist rotation of suspended end clamp assembly 60 (to counteract weight of mechanism) during tests involving bending of bone specimen 19.

To apply a twisting moment to a bone specimen 19 clamped within osteoclast 10 as herein described, the turnbuckle 75 is first tightened to pull the centering bridge 76 downwardly. As centering bridge 76 travels downwardly, it pulls down on load cell 83 and cable 77. By reason of the support of cable 77 on pulley 78, downward movement of bridge 76 results in an upwardly directed load on load cell 80. Hence, the torque bar 81 is pulled upwardly at one end and downwardly at the other, and, since it is fastened to the disk/clamp 65 as just described, the end of the bone specimen 19 within the suspended clamp assembly 60 is twisted clockwise for the arrangement shown. The degree of applied twisting moment is indicated by the outputs of load cells 80 and 83. All reaction points and connections are designed so that the entire torsion load mechanism 70 can be rotated 180° about a vertical axis thus allowing change of the direction of the torque from clockwise to counterclockwise.

Torque bar 81 comprises 1¼ inch square welded-seam steel tube approximately 14.50 inches long. The turnbuckle 75 is attached near the center of the centering bridge 76 via a slideably adjustable shackle to allow zero position (balancing) adjustment of load mechanism 70.

A humidity chamber 90 (see FIGS. 1 and 3) may be provided to enclose bone specimen 19 during test to provide an atmosphere of preselected composition therearound. Chamber 90 comprises a rectangular box constructed of plexiglass panels and polyethylene plastic sheeting, and is suspended by chains 91 or the like from trolley 32. The top and walls of the humidity chamber 90 were fabricated of five pieces of one-inch thick plexiglass held together with brass machine screws. Three narrow pieces span the top and clamp down on a sheet of polyethylene which is cut to allow the stabilizing cables 40 and the carriage suspension chain 50 of bending mechanism 30 to pass through. After a test specimen 19 is clamped into the osteoclast, the bottom of the chamber 90 is closed off by sliding two pieces of 2½ inch plexiglass into grooves cut along the bottom edges of the chamber 90 walls. Slots cut into the bottom pieces receive the stabilizing cables 40 and the clevis/yoke 37 of mechanism 30. Finally, the ends of the chamber 90 are closed either by sheets of polyethylene clamped to its walls or by pieces of thin polyvinyl chloride plastic taped around the chamber 90 ends.

A 2½ inch copper nipple 92 inserted in a hole in one of the chamber 90 sides, provides means to attach a source of humidified air (not shown) for supplying an atmosphere of desirable humidity surrounding bone specimen 19 during tests. During actual testing of a bone specimen 19 using osteoclast 10, as much as possible of the specimen 19 was exposed to an envelope of humid air of 80% to 90% saturation, and chamber 90 was sized accordingly.

Four dial indicators 28 (FIG. 2), 67 (FIG. 4), 54 (FIG. 3) and 87 (FIG. 4), provide means to measure deflections that represent, respectively, the displacements due to the bone 19 fixed end bending slope, suspended end bending slope, bending in the upper mid-diaphysal surface, and the twist at the suspended end caused by applied torsion. The two indicators 28 and 67 that measure bending slopes, sense, respectively, the pivotal displacements of the clamps 20 and 60. The fixed end slope indicator 28 is mounted to the inside flange of the upright beam 14 of frame 11 (see FIG. 2) and measures the deflections of the clamp 20 backplate 24 2¼ inches (5.71 cm) above the support (pivot) point (bolts 22). The suspended end slope indicator 67 is mounted on a small steel beam 68 welded to a steel C-clamp 69. The gage 67 is suspended from the bottom flange of the beam 12 and measures the slope deflections 9.09 cm above the support point. The bending deflection indicator 54 is bolted to a plate 55 welded to the bridge 31 of trolley 32. The bolt is adjustable vertically within a slot cut into the plate 55 to obtain the maximum travel of the probe for the various bone sizes. The probe of the indicator 54 includes a 7¾ inch (18.80 cm) extension in the form of an ell-shaped rod having the ell in contact with the lower surface of the bone specimen 19. Indicator 87 is positioned to measure the deflections created by the disk/clamp 65 as a bone specimen 19 is twisted under torsion, and is mounted directly to the aluminum yoke 63 with an aluminum bracket. Indicator 87 provides a measure of the deflections of the side of the clamp 60 as the disk 65 rotates in the racing of the yoke 63. The measurements are taken 4.24 cm above the center of rotation of the disk 65 (i.e., bolts 64).

Both the amount of bending load and/or the amount of torque applied to the bone specimen 19 may be determined using commercially available Wheatsone bridge type strain sensing load cells 36, 80, 83 and auxiliary electronic equipment (shown schematically in FIG. 1) connected thereto, including a manual switch and balance unit 95 and digital display 96. The torque applied is inferred by the tensile forces indicated by the load cells 80, 83 in the torsional load application mechanism 70. The concentrated bending loads applied by the rollers 39 in the bending carriage 38 are assumed to be one-half the tensile force indicated by the load cell 36 in the bending load mechanism 30. The display unit 96 generates the excitation current and voltage, and displays the signal returned in units of pounds force. The switch and balance unit 95 provides the means of selecting the desired load cell, refining the system calibration and balancing the bridges to indicate the desired initial loads.

The osteoclast of the present invention, as herein described in one representative embodiment thereof, was configured to facilitate the use of additional auxiliary equipment useful in the study of whole bone specimens. For example, in a representative study conducted using the invention, a plurality of strain gages (not shown in the drawings) were bonded to the bone specimens at preselected locations thereon to monitor stresses on the specimens during the application of loads.

The present invention, as hereinabove described, therefore provides a novel test device capable of simultaneously applying bending and torsional loads to a test specimen, and having particular utility for the studies of fracture patterns in bones. Though the device in the representative embodiment described herein is particularly suited to the testing of human long bones, it is clear that the invention may be alternatively used, with minimal modification, in the testing of other materials or structures. It is understood therefore that certain modifications to the invention as described may be made, as might occur to one with skill in the applicable field, within the intended scope of the appended claims. Therefore, all such embodiments contemplated hereunder have not been shown in detail. Other embodiments may be developed without departing from the spirit of this invention or from the scope of the appended claims.

We claim:

1. A test device configured to simultaneously apply bending and torsion loads to a test specimen, which comprises:
   a. a substantially rigid support frame comprising upper and lower support beams and a pair of upright lateral support beams;
   b. a first support pivotally mounted to one said lateral support beam for supporting a first end of said test specimen;
   c. a second support mounted between said upper and lower beams for pivotally supporting the second end of said test specimen, said second support being rotatable about an axis through said first and second supports;

d. torsion loading means, supported between said upper and lower beams and operatively connected to said second support, for applying torque to said specimen by rotation of said second support about said axis; and e. transverse loading means, supported between said upper and lower beams and intermediate said supports, for applying a load to said test specimen at a predetermined location therealong in a direction substantially perpendicular to said axis.

2. The device as recited in claim 1 further comprising:

a. first force sensing means, interconnecting said torsion loading means and said support frame, for measuring the amount of torque applied by said torsion loading means and providing an output signal proportional thereto; and b. second force sensing means, interconnecting said transverse loading means and said support, for measuring the amount of load applied by said transverse loading means and providing an output signal proportional thereto.

3. The device as recited in claim 1 further comprising means defining an enclosure for enclosing said specimen and said transverse loading means and means for supplying an atmosphere of predetermined composition to said enclosure.

* * * * *